(12) United States Patent
Jennings (10) Patent No.: US 7,240,545 B1
(45) Date of Patent: Jul. 10, 2007

(54) TEST APPARATUS FOR DIRECT MEASUREMENT OF EXPANSION AND SHRINKAGE OF OIL WELL CEMENTS

(75) Inventor: Scott Steven Jennings, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 10/575,408

(22) PCT Filed: Dec. 29, 2004

(86) PCT No.: PCT/US2004/044048

§ 371 (c)(1),
(2), (4) Date: Jan. 31, 2007

(87) PCT Pub. No.: WO2005/065411

PCT Pub. Date: Jul. 21, 2005

(51) Int. Cl.
G01F 17/00 (2006.01)
G01N 19/00 (2006.01)
G01N 33/38 (2006.01)

(52) U.S. Cl. .......................... 73/149; 73/429; 73/865.6; 73/866

(58) Field of Classification Search ............... 73/64.41, 73/149, 429, 865.6; 249/78, 82, 158; 264/40.5; 374/55, 56

See application file for complete search history.

(56) References Cited

U.S. PATENT DOCUMENTS

| | | | |
|---|---|---|---|
| 2,831,340 A * | 4/1958 | Crandall et al. ............ 374/56 |
| 2,978,781 A | 4/1961 | Shuman | |
| 3,239,880 A | 3/1966 | Oxel | |
| 3,574,281 A | 4/1971 | Casey et al. | |
| 3,779,085 A | 12/1973 | Rice | |
| 3,898,836 A * | 8/1975 | Clusener ..................... 374/56 |
| 4,122,704 A * | 10/1978 | Lutenegger et al. .......... 73/822 |
| 4,259,868 A * | 4/1981 | Rao et al. ..................... 73/597 |
| 4,377,087 A * | 3/1983 | Rodot ......................... 73/594 |
| 4,408,489 A | 10/1983 | Spangle | |

(Continued)

OTHER PUBLICATIONS

Chenevert, et al., Chemical Shrinkage Properties of Oilfield Cements Drilling Engineering, Mar. 1991, pp. 37-43.

(Continued)

*Primary Examiner*—Hezron Williams
*Assistant Examiner*—David A. Rogers
(74) *Attorney, Agent, or Firm*—Abelman, Frayne & Schwab (57) ABSTRACT

A test apparatus for the measurement of expansion and/or shrinkage of a cement test sample during curing under pressure and temperature conditions that simulate downhole oil well conditions isolates the test sample from a first fixed volume of incompressible pressurized liquid using a flexible barrier that forms a wall of a first chamber in a pressure vessel assembly. The first chamber is sealed by a movable piston. A second pressurizing medium is contained in a second chamber on the opposite side of the piston, and is in fluid communication with a pump, whereby the piston is pressure-balanced between the first and the second medium. The piston moves in a bore of the vessel assembly in response to changes in the volume of the test sample during curing and the amount of linear movement of the piston is detected by a sensor system that measures, correlates and transmits any change in the position of the piston as a change in the sample volume for display and recording.

24 Claims, 8 Drawing Sheets

U.S. PATENT DOCUMENTS

| | | | |
|---|---|---|---|
| 4,491,017 A | | 1/1985 | Iyer |
| 4,976,549 A | * | 12/1990 | Khan ........................ 374/56 |
| 5,009,512 A | | 4/1991 | Lessi et al. |
| 5,024,109 A | | 6/1991 | Romero et al. |
| 5,121,987 A | * | 6/1992 | Berg ........................ 356/496 |
| 5,465,609 A | * | 11/1995 | Romieu et al. ............... 73/38 |
| 5,487,307 A | | 1/1996 | Landgren et al. |
| 5,571,951 A | * | 11/1996 | Jamth ...................... 73/54.03 |
| 5,741,971 A | | 4/1998 | Lacy |
| 6,053,245 A | * | 4/2000 | Haberman ............ 166/250.14 |
| 6,070,465 A | | 6/2000 | Maki, Jr. |
| 6,527,438 B2 | * | 3/2003 | Zollinger et al. ............ 374/56 |
| 6,817,238 B2 | | 11/2004 | Go Boncan et al. |
| 2005/0039537 A1 | * | 2/2005 | Jensen et al. ................. 73/744 |

OTHER PUBLICATIONS

Gofrani et al, "CaO-and/or MgO-Swelling Cements: A Key for Providing a Better Annular Sealing?," SPE/IADC Drilling Conference, Feb. 1993, pp. 199-214.

Beirute et al., "Expansive and Shrinkage Characteristics of Cements Under Actual Well Conditions", Journal of Petroleum Technology, Aug. 1973, pp. 905-909.

Beirute, "True Expansive Characteristics of Commercially Available Expansive Cement Under Actual Well Conditions", SPE Annual Technical Conference and Exhibition, Oct. 1976, pp. 1-8.

International Search Report, Oct. 13, 2005.

International Preliminary report on Patentability; May 4, 2006.

\* cited by examiner

TEST APPARATUS FOR DIRECT MEASUREMENT OF EXPANSION AND SHRINKAGE OF OIL WELL CEMENTS

FIELD OF THE INVENTION

The invention relates to a laboratory test method of and an apparatus for determining shrinkage and expansion in cement test samples and specifically to a laboratory test method of and apparatus for measuring volume changes in cement compositions that are subject to high temperatures and pressures.

BACKGROUND OF THE INVENTION

During oil and gas well drilling operations, it is often necessary to seal the space between the outer casing string, or pipe and the rock formation through which the drill has passed in order to prevent the undesired flow of fluids including gas, oil and incompressible media such as water. Undesirable fluid flow can be in an upward direction either along the well pipe casing or downwardly where it might be dissipated into the formations below and/or mixed with other fluids.

A variety of compositions are pumped into the bore hole adjacent to the rock formation for the purpose of providing a tight seal between the metal well casing pipe and the surrounding irregular rock surface. The cement composition is disposed in the form of highly flowable slurry that will easily pass downwardly through the irregular annulus formed by the casing and surrounding rock. Its particular formulation will depend upon a number of parameters related to the local conditions. Various mechanical devices are available to provide a mechanical block at the lowermost portion of the bore hole in order to stop the flow of the cement slurry.

The cementing can be required at considerable depths so that the slurry composition is subjected to extremes of high pressure and temperature as it is curing and forming a monolithic mass in the irregular annulus. It is well known in the art that, under these conditions, various cement compositions will either shrink or expand to some extent. Since the cement compositions are often formulated at the site of the well in order to accommodate the specific subterranean conditions present and the downhole rock formations, it is desirable to know in advance how a particular "custom" cement composition will perform with respect to expansion/ shrinkage under the subterranean conditions of setting and curing.

Test apparatus for cement samples vary in their purpose and methods. Cement testing apparatus that use pistons to directly pressurize and measure the changes in test samples can introduce errors into measuring test sample shrinkage. These errors occur when portions of the cement test sample build up between the edges of the piston and vessel assembly wall and prevent or slow the downward movement of the piston. This can result in an inaccurate pressurization and measurement of the shrinkage by the pressurizing piston during the test.

It is therefore a principal object of the invention to provide a laboratory test method of and an apparatus for measuring the expansion and/or shrinkage of cement slurry as it sets and cures under pressure and temperature conditions simulating those in the well in which the particular cement composition is to be utilized.

It is another object of the invention to provide a test apparatus that is reliable, sturdy and readily reused.

It is a further object of the invention to provide a pressure and temperature test apparatus that uses a flexible diaphragm to isolate the test sample and an incompressible medium for pressurizing the test sample to overcome the likelihood of introducing errors into the measurement of the changes in the test sample.

It is still another object of the present invention to measure shrinkage and expansion of the test sample by the change in volume of the test sample.

It is another object of the present invention to provide a floating piston and a measuring device that are pressure balanced to the pressure applied to the test sample such that when the volume of the test sample changes, the piston changes position and the measuring device determines the amount of the volume change of the test sample by the change of position of the piston.

Yet another object of the invention is to provide a laboratory test method and apparatus that is capable of measuring both expansion and shrinkage of a cement composition sample for which there is no previous data as to whether the cement composition is likely to shrink or expand upon curing.

SUMMARY OF THE INVENTION

The above objects and other advantages are provided by the test apparatus for the measurement of the expansion and/or shrinkage of sealing compositions, e.g., cement, used in downhole oil well applications. The test apparatus of the invention includes a modified ultrasonic cement analyzer cell sleeve or pressure vessel assembly, a pressure intensifier or pump, thermal test instrument and a computer. A suitable unmodified cell sleeve is commercially available from Chandler Engineering Company of Tulsa, Okla., www.chandlereng.com. As used herein, the term "pump" includes a pressure intensifier or other device that is capable of pressurizing the associated fluid or chamber.

The vessel assembly receives and isolates the test sample, an incompressible pressurized medium and a second pressurizing medium in three separate volumes in a pressure vessel assembly housing. The test sample is sealed in a sample containing portion at one end of the test vessel using a flexible barrier seal that is placed in contact with the exposed surface of the sample. The incompressible pressurized medium is placed between the flexible seal and a piston. The piston isolates the second pressurizing medium in the end of the test vessel housing opposite the sample containing portion. In the preferred embodiment, pressure is applied to the second medium, and transmitted by the piston to produce an equivalent pressure in the incompressible medium, which is applied through the flexible seal to the test sample. The piston is thereby pressure balanced between the pressurized medium and the pressurizing medium and moves in response to volume changes in the test sample.

The piston has an initial position when pressurizing the fixed volume of the first pressurized medium. The subsequent travel of the piston in the vessel assembly due to the curing, expansion and/or shrinkage of the test sample is sensed in one preferred embodiment by a digital measuring device, such as a linear variable displacement transducer (LVDT) coupled to an expansion/shrinkage interface device, i.e., a computer. The volume of the second pressurizing medium is varied in response to the change in volume of the test sample to maintain the test sample at the desired pressure level.

In a preferred embodiment, the temperature of the test sample is increased to simulate downhole conditions as determined from actual measurement in the field and based upon the locations where the test material, e.g., cement, is to be used. Heating of the pressure vessel assembly can be by immersion in an oil bath, radiant sources, induction heating, electric coils and other means known to the art.

Temperature and pressure test parameters are set and the actual test data is monitored during the test process by processor/controller. As the cement test sample undergoes any volume changes during high pressure and temperature testing, the resulting movement of the incompressible pressurized medium and piston is recorded by a sensor assembly that includes a measuring device, such as the LVDT, and transmitted to the processor/controller.

The controller preferably includes a programmable computer for inputting sample identification information, starting and completion times and the test profile. The controller provides for automated or manual monitoring and controlling of the test process.

A separate computer is preferably coupled to the controller that receives, formats, stores, displays and/or processes the recorded test data of the test sample cement composition. The computer uses the data from the measuring device to calculate the shrinkage or expansion of the test sample as a percent of change in the original slurry volume. The computer as defined herein can include data transfer, recording, control inputs, calculation, analysis and printing functions using commercially available standard and/or proprietary programs and formats.

In operation, the cement slurry test sample fills and is sealed by the flexible barrier seal in a sample containing portion of the vessel assembly housing. The pressurized medium, which can be water, oil, hydraulic fluid or the like, is added to the first chamber formed by the specific seal and the floating piston. The second chamber is filled with the pressurizing medium on the opposing side of the piston.

A pump pressurizes the second medium and the piston transfers the pressure to the first pressurized medium and, through the flexible barrier seal, the test sample. Piston seals prevent passage of the fluids on either side and the piston is thus pressure balanced between the fluids in the first and the second chambers. The pressure balanced piston floats between the opposing and equal pressures such that volume changes of the test sample displace the fixed volume of the first pressurized medium, the piston and second medium. The sensor system detects the amount of displacement of the piston in the vessel assembly and transmits the data to the computer.

A test apparatus for the measurement of a change in volume due to the expansion and/or shrinkage of a curable test sample during curing of the sample from a viscous to a solid state. The apparatus comprises (a) a pressure vessel assembly housing having a sample containing portion for receiving the test sample and providing an exposed sample surface; (b) a flexible barrier seal extending across the sample surface for isolating the test sample in the sample containing portion; (c) a piston slidably mounted in a bore in the vessel assembly housing and spaced apart from the barrier seal to define a first fluid-tight chamber for receiving a volume of a first incompressible pressurized fluid medium; (d) a second chamber defined by the opposite wall of the piston and the vessel housing; (e) a pressurizing fluid reservoir external to the housing and in fluid communication with the second chamber; (f) a pump in fluid communication with the second chamber and reservoir such that a fluid in the second chamber pressurized by the pump exerts a corresponding pressure on a sample in the sample containing portion via the piston; and (g) a sensor assembly operably connected to the piston for measuring changes in the position of the piston resulting from the change in volume of the test sample.

The first pressurized incompressible medium and the second medium are preferably liquids. The external fluid reservoir includes a reservoir fluid level indicator with markings that correlate to the change in volume of the test sample during curing.

The test apparatus sensor assembly includes a core and a measuring device with a coil whereby the movement of the piston is communicated to core movement that is sensed by the coil. Heating and cooling means are employed to raise and lower the temperature of the sample in the test apparatus. A controller contains test parameters and receives and records test data from the test apparatus. Test parameters comprise pressure temperature, the rate of change of pressure and temperature, and time. The controller includes an indicator for the initial position of the piston in the bore.

A test apparatus for the measurement of the expansion and/or shrinkage of a test sample, which comprises a vessel assembly housing, one end of which includes a sample receiving portion. A flexible seal extends across the sample receiving portion to isolate a sample placed therein from the rest of the housing. A movable piston sealingly mounted in a bore of the vessel assembly housing and isolating a first pressurized chamber from a second pressurizing chamber in the housing. The first chamber is defined by the flexible seal and one face of the piston and is provided with an incompressible fluid. The second chamber is defined by an opposing side of the piston and the end of the housing opposite the sample receiving portion. A source of pressurizing fluid external to the housing is provided that is in fluid communication with the second chamber. A sensor assembly is included that is responsive to movement of the piston and an associated display and recording means for measuring the linear movement of the piston.

The sensor assembly has a mechanical linkage that extends from the piston through the second chamber to a coil. The piston is a floating piston that is pressure-balanced between the incompressible medium in the first chamber and the second medium in the second chamber. The piston moves in the bore of the vessel assembly housing in direct correlation to changes in the volume of the test sample. The movement of the piston in the bore is detected by a measuring device. The measuring device indicates the displacement of the piston by the displacement of the pressurized fluid in response to an increase or decrease in the volume of the test sample by the displacement of the flexible seal. The functions of the sensor assembly are directed by a computer integrated with the test apparatus. The test apparatus includes means for heating and cooling the test sample in the vessel assembly to simulate downhole conditions.

The method of the invention for measuring the expansion and/or contraction of a curable test sample broadly comprehends the following steps: A flowable test sample is isolated in a rigid sample receiving portion of a test vessel. A flexible seal is secured over an exposed surface of the test sample in the sample receiving portion so that the opposing side of the seal is in contact with a fixed volume of an incompressible pressurized liquid that is maintained in a first chamber in the test vessel by a proximal face of a movable piston that is sealingly positioned in a bore formed in the test vessel. A force is provided by a pressurized fluid in a second chamber in the test vessel to a distal face of the piston. The liquid in the first chamber and the fluid in the second chamber are isolated from each other. The measurement of any movement of the piston during the curing of the sample is correlated to a volumetric change of the sample.

The method includes filling the sample receiving portion of the vessel assembly with a curable cement test sample and heating and/or cooling the test sample in accordance with predetermined parameters. The air entrained in the test sample is removed before securing the flexible seal of this sample over the surface. Air is excluded from the first and second chambers and from the liquid and fluid contained in said respective chambers.

The pressure of the pressurizing fluid is substantially constant during a test cycle. Measuring the displacement of the piston includes detecting the amount of displacement of the piston using an LVDT. The data on the change of volume of the test sample is transmitted to an expansion/shrinkage interface. The correlation of the piston's movement includes transmitting signal data to a computer for at least receiving, processing and recording test data.

In an alternative embodiment, the second pressurizing medium is also an incompressible liquid and the volume change of the second medium due to movement of the piston is used to provide a direct measurement in the change in volume of the test sample.

BRIEF DESCRIPTION OF THE DRAWINGS

Preferred embodiments of the invention are described below with reference to the drawings, wherein like numerals are used to refer to the same or similar elements.

DETAILED DESCRIPTION OF PREFERRED EMBODIMENT

Figure 1:
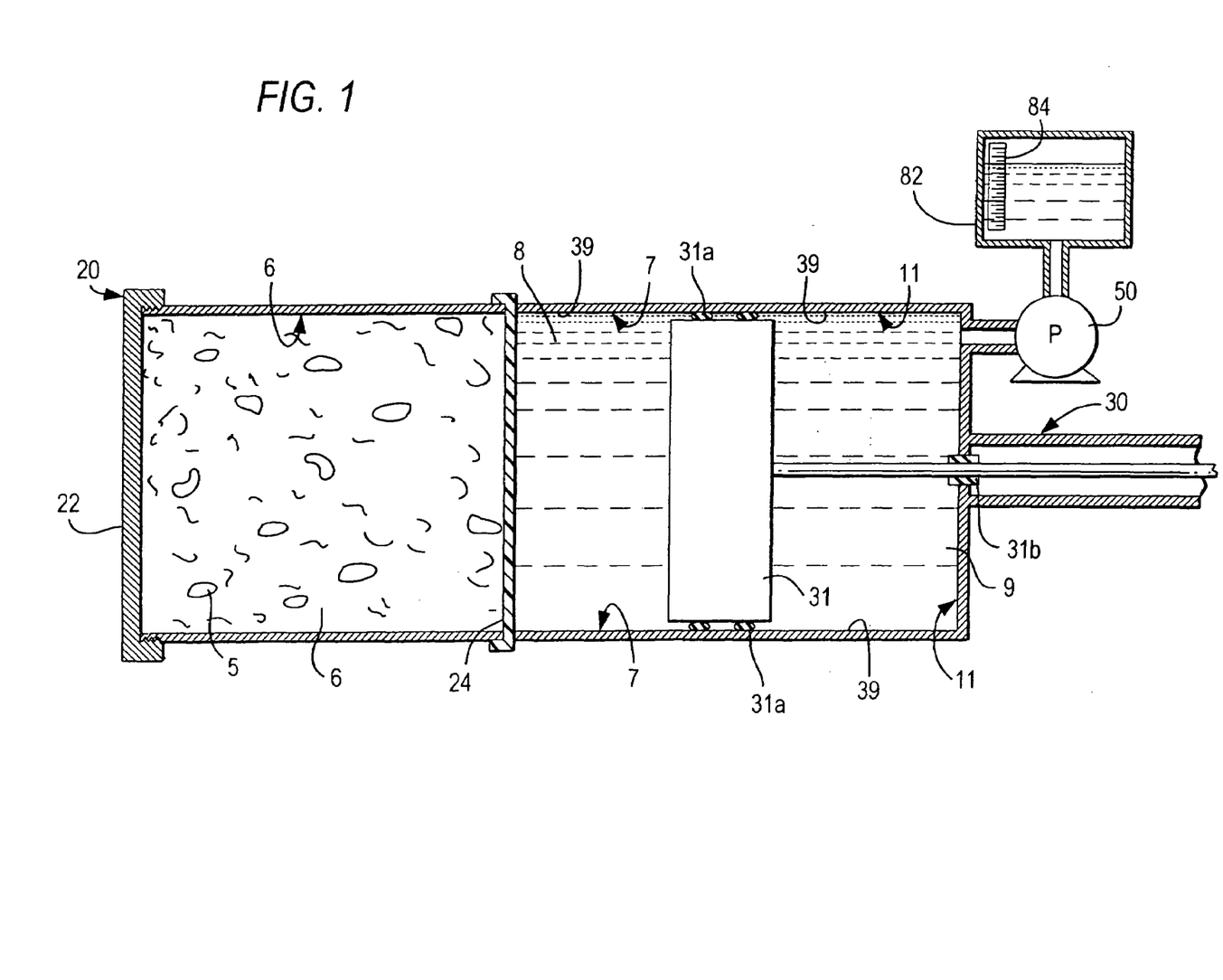
FIG. 1 is a simplified schematic diagram of one embodiment of a pressure vessel assembly housing of the invention for direct measurement of the expansion and shrinkage of curable samples.

With reference to FIG. 1, a simplified schematic view of a pressure vessel assembly housing 20 is shown with a fresh sample 5 filling a sample containing portion 6 with its inner surface covered securely by a flexible barrier seal 24 and the housing 20 closed by threaded end cap 22. A first pressurized chamber 7 contains pressurized liquid 8, which is preferably water. All entrained air has been removed from the sample 5 and air has been excluded from the liquid in the first chamber 7. A piston 31 with seals 31a, which can be O-rings, is movably positioned in a bore section 39 of housing 20. A second pressurizing chamber 11 is formed in the end of housing 20 and contains a pressurizing fluid 9 that is in fluid communication with external reservoir 82. A pump 50 is activated to maintain the desired pressure on the preferably incompressible pressurizing fluid in second chamber 11.

With continuing reference to FIG. 1, a sensor assembly 30, includes a direct mechanical connection to the distal face of piston 31 which can extend in the second pressurizing chamber 11 or, alternatively, through a housing seal 31b into a separately defined volume. The proximal end of the sensor assembly 30 includes means for measuring the linear movement of the piston 31 in its bore 39 and, preferably, converting that measure to a correlated value of the change in volume of the sample during curing and at least in its final state.

As also shown in FIG. 1, the reservoir 82 includes a gauge 84 or other level indicating means, such as a sight glass (not shown), to indicate a change in the level of the preferably liquid in this portion of the system. In the starting position at the beginning of the test protocol, the pressurized system is in equilibrium, i.e., the pressure applied on the sample through the flexible barrier seal by the liquid in the first chamber is equal to the pressure of the fluid in the second chamber and the piston is not moving. When the volume of the sample changes due to physical changes that occur during curing or testing, the change is transmitted through flexible barrier 24 and produces a change in the pressure of the liquid in the first chamber. In order to equalize the pressure in the two chambers, the piston moves, either towards a shrinking sample or away from an expanding sample. Any movement of the piston is conveyed by the sensor system to the measurement means.

Figure 2:
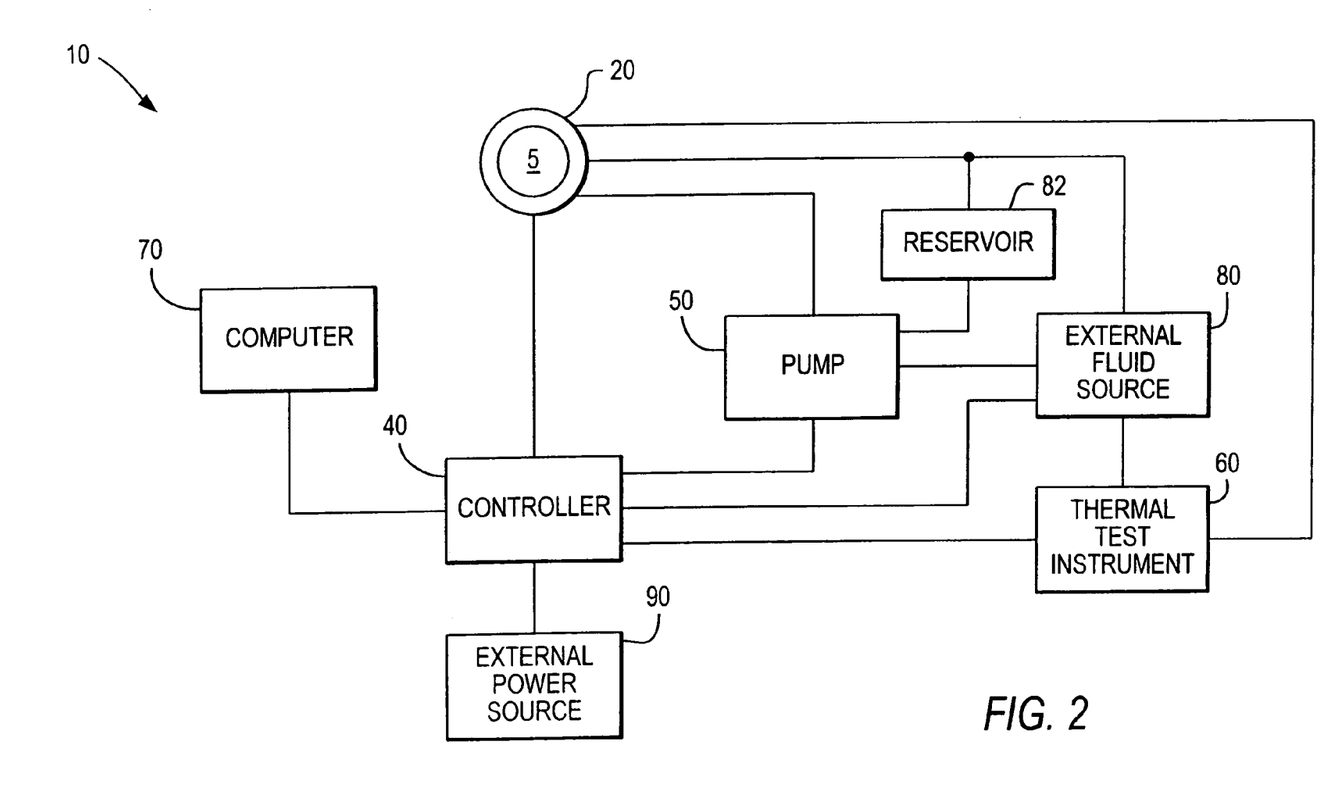
FIG. 2 is a schematic diagram of one embodiment of a test apparatus of the invention for direct measurement of the expansion and shrinkage of oil well cements for use with the vessel assembly of FIG. 1.

Referring to FIG. 2, a simplified schematic diagram illustrates one preferred embodiment of a test apparatus 10 for the measurement of the expansion and shrinkage of oil well cements in simulated downhole oil well environments, including high temperature and high-pressure conditions. Test apparatus 10 measures, records, analyzes and displays the changes in volume of a cement slurry test sample 5 as the sample sets and cures under the specified test conditions. Test apparatus 10 includes a vessel assembly 20, an controller 40, a pump 50, and a thermal test instrument 60. An external fluid source 80 and an external power source 90 are also connected to test apparatus 10.

Figure 3:
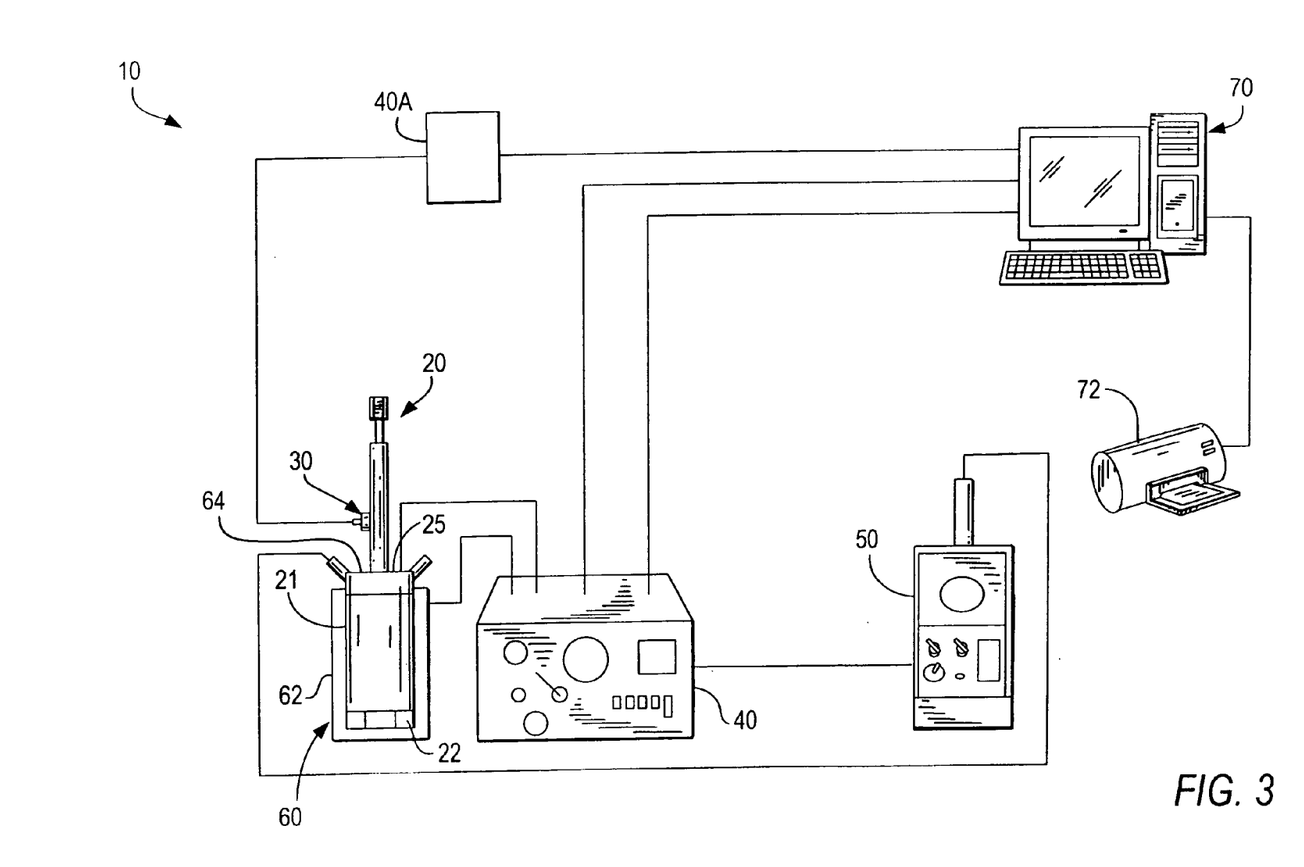
FIG. 3 is a simplified schematic view of a second embodiment of the test apparatus of FIG. 2.
Figure 4:
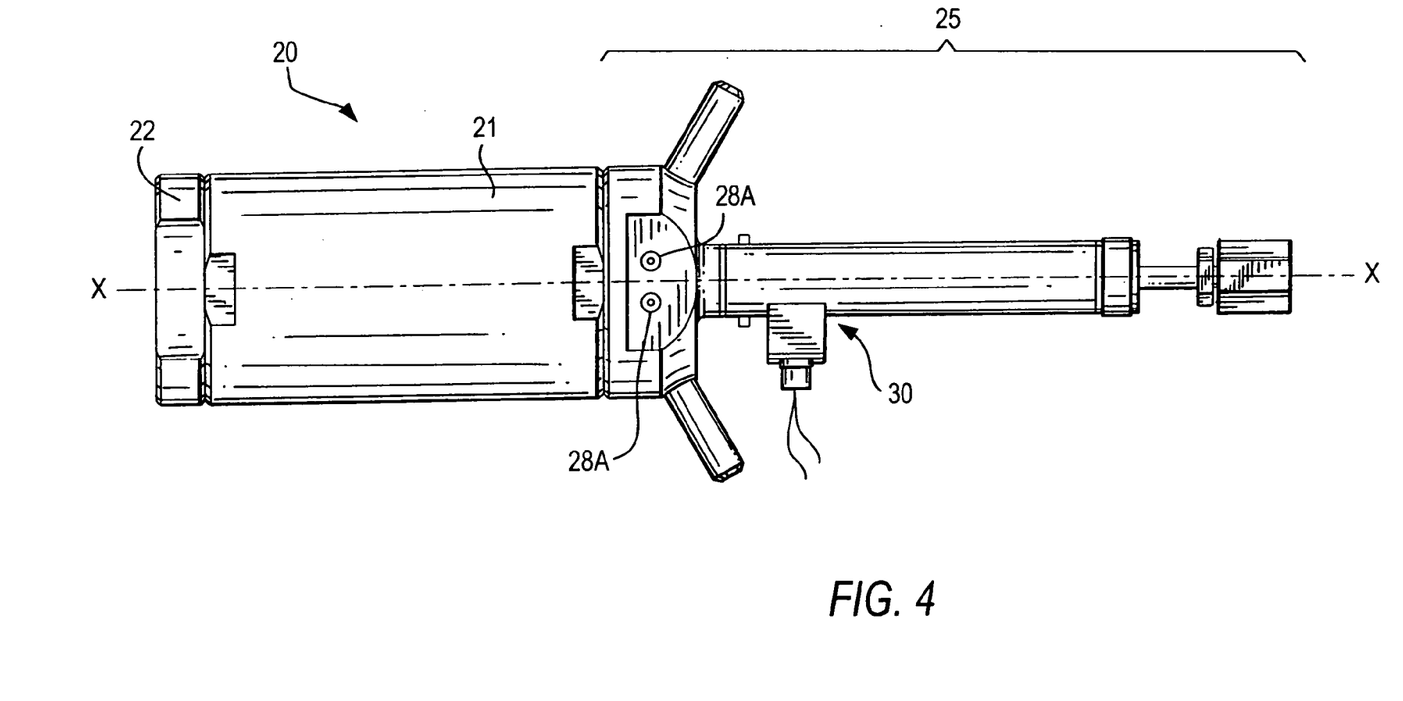
FIG. 4 is a side elevational view of a vessel assembly of the test apparatus of FIG. 3.
Figure 5:
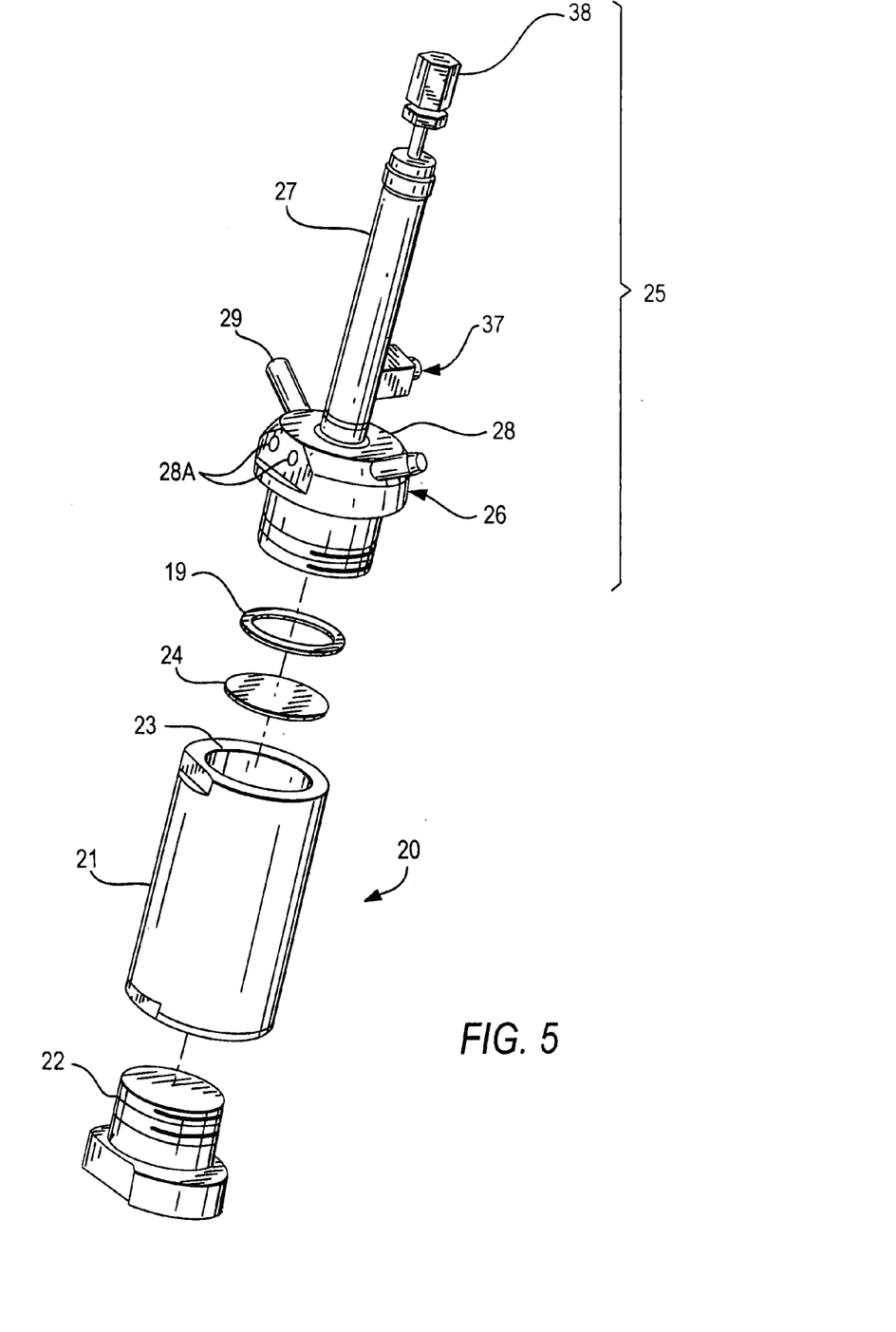
FIG. 5 is a front and side perspective view, partially exploded, of the vessel assembly of FIG. 4.

As shown in one preferred embodiment of FIGS. 3, 4 and 5, vessel assembly 20 includes a tube 21, bottom plug assembly 22, a top plug assembly 25 and a sensor system 30. Test vessel 20 is a pressure vessel defining an interior space or cavity for sustaining pressure ranges from ambient conditions to approximately 10,000 psig (69.1 Mpa) from pump 50 in combination with temperature ranges from ambient conditions to approximately 400° Fahrenheit from thermal instrument 60. Test Apparatus 10 includes a data interface 40A and a computer 70. Data interface 40A provides a read function of the data output from test vessel 20 and computer 70 processes the data and provides a display and printer.

Referring now to FIGS. 4 and 5, tube 21 preferably has an annular wall that defines a bore 23 having a centerline aligned with a longitudinal axis-X. Connectors on the opposing ends of tube 21 removably connect with bottom plug assembly 22 and top plug assembly 25. It is understood that the reference terms of top and bottom of vessel assembly 20 are for directional and explanatory purposes and independent of any operational orientation.

As shown in FIGS. 1, 3, 5 and 6, vessel assembly housing or test vessel 20 defines an interior cavity to receive, isolate and measure any volume changes in the cement slurry test sample 5 under downhole conditions of temperature and pressure. The pressurized interior cavity of vessel assembly 20 is divided into three separate volumes. A first volume or sample containing portion 6 receives test sample 5, a second volume or first pressurized chamber 7 receives an incompressible medium 8 and a third volume or second pressurizing chamber 11 receives a second medium 9. Test sample 5 preferably has a volume of at least approximately 200 ml. Medium 8 and medium 9 are preferably separate volumes of incompressible fluid with medium 9 providing a pressurizing force to medium 8 via sealed movable piston 31.

The sample containing portion of vessel assembly 20 extends along the annular wall 23 from bottom plug 22 to diaphragm 24 that is positioned as a flexible impermeable barrier in tube 21 that separates test sample 5 and/or sample containing portion 6 from first incompressible medium 8 in the first chamber 7. A sealing shoulder on an inner side of the tubular wall of tube 21 receives the periphery of diaphragm 24 and a sealing ring 19.

Diaphragm 24 can be fabricated of any high temperature rated flexible rubber composition or polymeric material, i.e., a fluoroelastomer, that is compatible with the cement, the medium 8, and the pressure and temperature conditions imposed on the test apparatus 10. In one preferred embodiment, diaphragm 24 is fabricated from 75 durometer Viton® and has a thickness of approximately 0.060 inches. In still another preferred embodiment, diaphragm 24 can be used in conjunction with and/or include a 0.75 to 1.0 inch OD stainless steel disk approximately 0.03125 inches thick. The disk is positioned between the top of test sample 5 and diaphragm 24 to minimize any surface irregularities.

Top plug assembly 25 includes a plug 26 and a tube 27. As shown in FIGS. 4 and 5, plug 26 has high-pressure ports 28 and 28A, handles 29 and a bore 39 aligned with bore 23 of tube 21. A first end portion of top plug assembly 25 sealingly mates with tube 21 and an opposing second end portion includes tube 27. High-pressure ports 28 provide access to the first chamber 7 for adding and releasing incompressible medium 8. High-pressure ports 28A provide access to the second chamber 11 for adding, releasing and pressurizing medium 9. Removable threaded handles 29 are positioned on plug 26 for ease of assembly and disassembly of top plug assembly 25 with tube 21. A portion of bore 39 defines the first chamber 7 for the receiving incompressible medium 8. The remaining portion of bore 39, on the opposing side of piston 31, and tube 27 define the second chamber 11 for receiving second medium 9.

Tube 27 defines a passageway 27A that is in fluid communication with the second chamber 11 in bore 39 on one end and a terminal end cap 38 on the opposing end. A port 37 includes external connections for sensor system 30 and is preferably in fluid communication with passageway 27A.

Sensor system 30 is housed in top plug assembly 25 and measures volume changes in test sample 5 during test operations. The measured changes of the volume of test sample 5 are transmitted to data interface 40A and computer 70 for functions such as formatting, recording, calculation and display. Sensor system 30 includes a piston 31 and a measuring device 34. Piston 31 has a rod 32, a crown 33 and moves in bore 39 in plug 26 in response to changes in the volume of test sample 5. Piston 31 includes one or more seals or O-rings 31a that in combination with crown 33 provide a sealing interface or wall in bore 23 separating medium 8 and medium 9 positioned in the first 7 and second 11 chambers of vessel assembly 20, respectively.

Rod 32 is an elongate cantilever beam that is preferably rigid and extends from the side opposing crown 33 of piston 31 through a portion of bore 39 and into the passageway 27A of tube 27. Measuring device 34 includes a core 35 positioned on a terminal end of rod 32 that moves linearly inside a coil assembly 36. Coil assembly 36 generates a signal in response to the movement of core 35 and transmits that signal to data interface 40A as data measuring the change in position of core 35 that corresponds to a volume displacement of test sample 5. Piston 31, rod 32 and core 35 can be monolithically formed as one component and/or integrally connected together as a single assembly.

In one preferred embodiment of measuring device 34, core 35 and coil assembly 36 define a linear variable displacement transducer, or LVDT, that is positioned in passageway 27A of tube 27. In this preferred embodiment, the LVDT is pressurized as part of the second chamber 11. Measuring device 34 has a range of measurement of approximately +/−0.5 inches and can provide a continuous data output to data interface 40A and/or computer 70 for the recording, tracking and calculating volume changes of test sample 5. Measuring device 34, however, can be any device, including a precision device, capable of measuring the movement of piston 31, such as an optical scanner or an accelerometer or other mechanical sensor that can be at least partially positioned external to the second chamber 11 and/or vessel assembly 20.

Incompressible medium 8 is positioned between diaphragm 24, an impermeable flexible seal, and piston 31. Incompressible medium 8 preferably fills the first chamber 7 and remains a fixed volume during the testing process. Piston 31 pressurizes incompressible medium 8, which pressurizes test sample 5 through diaphragm 24.

Medium 9 is sealed on the opposing side of piston 31 in top plug assembly 25 by the one or more O-rings 31a and a terminal end 38 of the passageway 27A of top plug tube 27. Pressure is supplied to medium 9 through one of high-pressure ports 28A. When the pressure on medium 8 by piston 31 and medium 9 is balanced, piston 31 is free to float along bore 39 in response to the varying volume of test sample 5 during the test profile.

Thus, balanced pressure levels in the preferred embodiment, as defined herein, are understood to mean balanced or substantially identical pressure levels on test sample 5 and the opposing sides of piston 31. In the present invention, changes in the volume of test sample 5 displace incompressible medium 8 in the first chamber 7 that results in a direct displacement of piston 31 and second medium 9.

Figure 7:
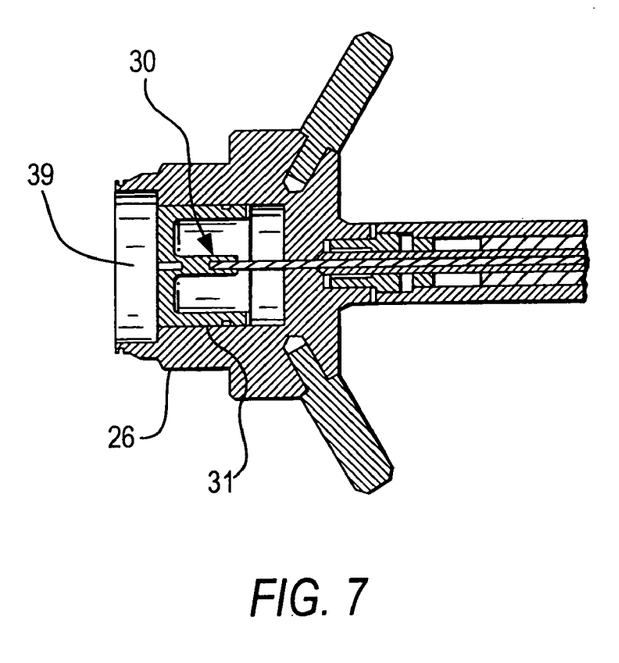
FIG. 7 is a cross-sectional view of a portion of a top plug assembly of the vessel assembly of the test apparatus showing a piston located at a zero shrinkage/expansion position.
Figure 8:
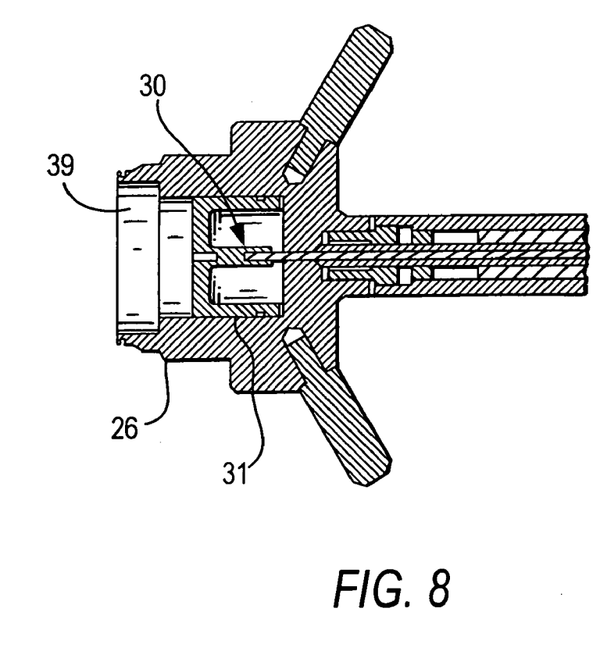
FIG. 8 is a cross-sectional view of the top plug assembly of the test apparatus of the present invention showing the piston located at a maximum expansion position.
Figure 9:
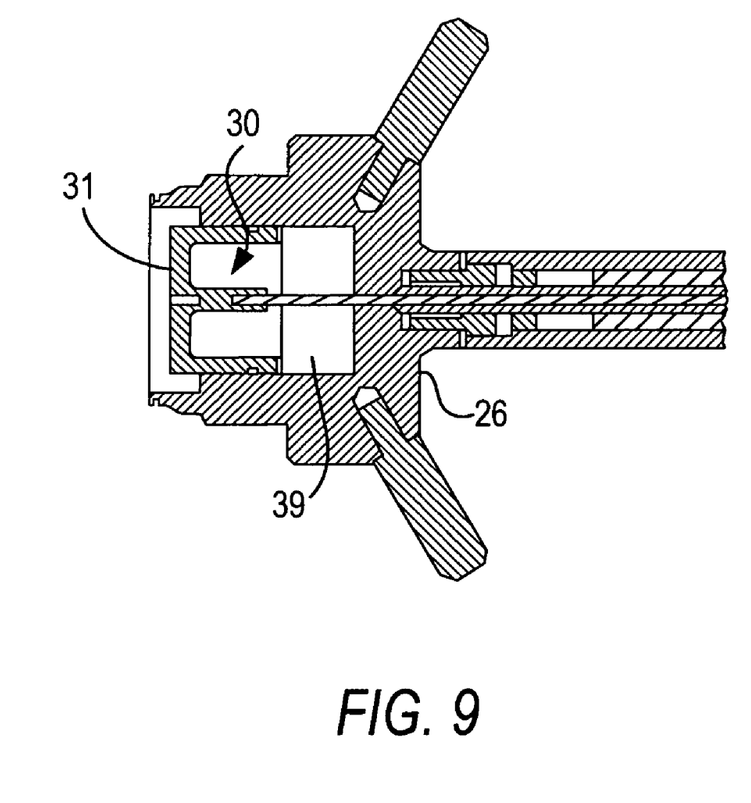
FIG. 9 is a cross-sectional view of the top plug assembly of the test apparatus of the present invention showing the piston located at a maximum shrinkage position.

The internal volume of plug assembly 25 is sufficient to accommodate the movement of piston 31 along bore 39 of vessel assembly 20 for an expansion of approximately 10% (20 ml) and a shrinkage of approximately 16% (32 ml) based on the original volume of test sample 5 as shown respectively in FIGS. 7 and 9. It is recognized, however, that vessel 20 can accommodate varying test sample sizes and the volume of plug assembly 25 can be similarly sized to accommodate greater or lesser ranges of change in volume of the test sample.

Referring now to FIGS. 3 and 4, in one preferred embodiment, test vessel 20 is a modified 4268ES cement expansion/shrinkage cell used as an accessory with a pressure intensifier or pump 50 manufactured by Chandler Engineering of Tulsa, Okla. The modifications to provide the test vessel 20 are within the skill of the art.

As shown in FIGS. 2 and 3, controller 40 sets and monitors test parameters such as the temperature and pressure ramping rates and dwell times for test sample 5 in vessel assembly 20. Controller 40 is a computerized device using one or more software programs to establish the test parameters. Controller 40 can provide both manual and automatic control of the test parameters of a test profile including, for example, the pressure applied by pump 50 and the temperature applied by thermal instrument 60 to test sample 5 in vessel 20. Controller 40 is coupled with vessel assembly 20, pump 50, thermal test instrument 60 and computer 70.

A data interface device 40A is provided for receiving, reading and/or forwarding data from vessel assembly 20. For example, controller 40 receives data such as the position of piston 31 in plug 26 using one or more data interface 40A devices for reading the data. Measuring device 34 senses the initial position of piston 31 and forwards that data to data interface 40A computer display. As shown in FIGS. 3 and 7-9, controller 40 can indicate the location of piston 31 in bore 39 such as located in the mid-range, top (maximum expansion) or bottom (maximum shrinkage) of its range of movement. Piston 31 is preferably initially positioned in the mid-range area to accommodate an approximately equal range of expansion and shrinkage, but the position indicator is sufficiently flexible to position piston 31 at the bottom or top of the range of movement accommodate test samples having known or suspected disproportionately large ranges of shrinkage or expansion. Data interface 40A can be a stand-alone device that is connected to, or an integral subassembly of controller 40 and/or computer 70.

In one preferred embodiment of controller 40, a Model 5285 Static Gel Strength Analyzer or a Model 4265 Ultrasonic Cement Analyzer provide the test control functions such as the programmable temperature and pressure controls for test apparatus 10. The 4268ES Cement Expansion/Shrinkage Cell is intended for use as an accessory to the Model 5285 Static Gel Strength Analyzer or Model 4265 Ultrasonic Cement Analyzer, the above items also being manufactured by Chandler Engineering.

In one preferred embodiment, pump or pressure intensifier 50 provides a hydraulic pressurizing force through one of high-pressure ports 28A for simulating a range of pressure conditions up to and including the high-pressure environments encountered in deep formations. The range of pressure levels and durations provided by pump 50 are set by controller 40 for a given test profile for test sample 5. This includes providing balanced pressure levels on incompressible medium 8 and medium 9 by adjusting the volume of medium 9, as required to maintain the desired pressure level on incompressible medium 8 and test sample 5. Controller 40 and pump 50 provide a closed loop feedback system for applying pressure to medium 9 of test vessel assembly 20. Pump 50 is connected with external fluid reservoir.

Pump 50 is preferably a piston-type intensifier, provides an approximate compression ratio of 100:1 and uses air pressure to create hydraulic pressures of up to a maximum of approximately 10,000 psig or 69 Mpa within vessel 20. In one preferred embodiment, pump 50 is a pressure controller Model 6265-I Intensifier Assembly manufactured by Chandler Engineering. It is understood, however, that pump 50 can be any high pressure pump that can provide the pressure levels and accuracy required for use in test apparatus 10.

Thermal test instrument 60 includes a thermal device 62 and a temperature sensor 64 and uses controller 40 to set temperature ramping rates and dwell times. Thermal device 62 provides a maximum temperature of approximately 400° F. (204° C.). In one preferred embodiment, thermal device 62 is a thermal sleeve that is placed around vessel assembly 20 to provide for the heating and cooling of sample 5. It is to be understood that thermal device 62 can be any heating and cooling means or combination of means such as electrical, a fluid based system or a temperature-controlled test chamber.

Temperature sensor 64 is preferably positioned in one of ports 28 and provides a closed loop feedback to controller 40 on the temperature environment in test vessel 20. Temperature sensor 64 is preferably a thermocouple, but it is understood that sensor 64 can be any type of temperature sensing device that can withstand pressures up to about 10,000 psi.

Computer 70 is an electronic device that receives, performs logic and mathematical operations and displays data. Computer 70 can display data via a screen and receives and records test data such as actual temperature, pressure and displacement measurements. A printer 72 is preferably connected to computer 70. Computer 70 can also provide analytical tools and standard forms of data storage for the analysis of volume changes in sample 5 and, for example, the rate of the volume changes. In one preferred embodiment, computer 70 includes a Model 5270 Data Acquisition and Control System for data retrieval, analysis and storage produced by Chandler Engineering. Computer 70 and/or controller 40 also preferably monitor the status of external source of fluid 80 and external power source 90.

External fluid source 80 includes a source of filtered, pressurized incompressible medium 8 and/or 9 at 5-150 psig (0.34-10.4 bar); a coolant, such as water or an ethylene glycol solution; and filtered and dry compressed air at 75-125 psig (5.2-8.6 bar). Pump 50 is coupled with air as for pressurization and is also preferably coupled to vessel assembly 20 via a reservoir 82 for the pressurization of medium 8 and medium 9. A drain or vessel is provided to receive any hot fluids discharged by test apparatus 10.

External power source 90 provides power for the individual test equipments of apparatus 10 such as vessel assembly 20, controller 40, data interface device 40A, pump 50, thermal instrument 60, computer 70 and fluid source 80. Power source 90 can be directly coupled to the individual assemblies of test apparatus 10 or through controller 40 or data interface device 40A. External power source 90 can include an uninterruptible power supply.

Figure 6:
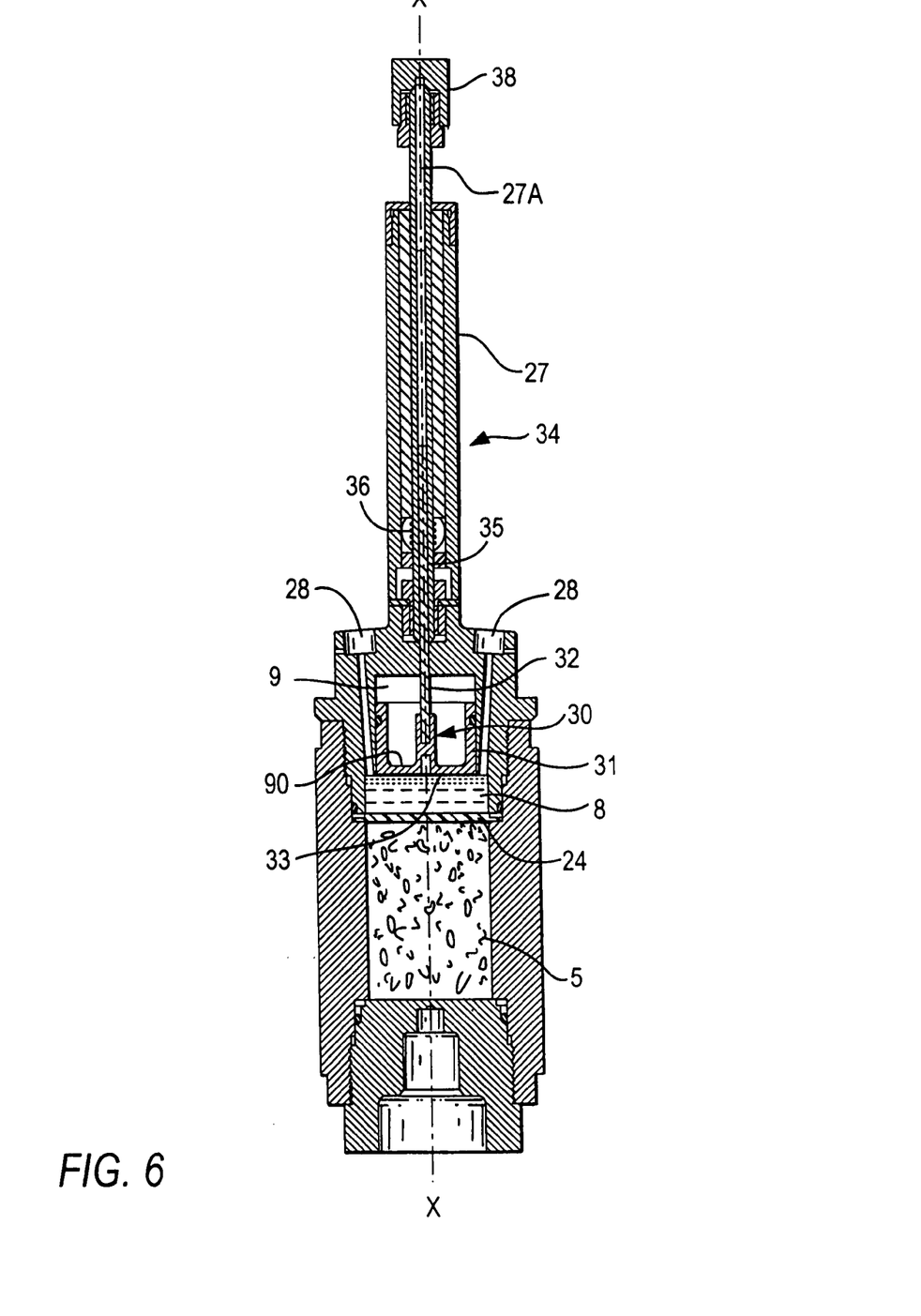
FIG. 6 is a cross-sectional view of one embodiment of the vessel assembly of the present invention.

Referring now to FIGS. 2, 3 and 6, in an alternative embodiment of sensor system 30, pump 50 provides a balancing pressure to incompressible medium 8 in the first chamber 7 and second medium 9 in the second chamber 11 such that there is a balance of pressure on piston 31 between the opposing and equal pressures on medium 8 and medium 9. The volume of second medium 9 is adjusted as required to maintain the desired pressure on test sample 5.

In another alternative embodiment, medium 9 is a pressurizing device positioned in the second chamber 11 that applies a pressure to floating piston 31. The device can include, for example, linear actuators or electro-mechanical devices that can maintain a desired pressure level on piston 31 and incompressible medium 8 while retaining the free movement of piston 31 in response to changes in volume of test sample 5.

In an alternative embodiment of controller 40 and data interface device 40A, the functions performed by controller 40 and data interface device 40A are performed by one or more software programs and/or hardware on computer 70. Computer 70 can then be used for the operational control of test apparatus 10, including the setting of test parameters such as test profiles and the receiving of actual test data. As described previously, computer 70 can also provide manual control of individual equipments such as vessel assembly 20, pump 50 and thermal instrument 60. It is understood that controller 40 and data interface device 40A, in this embodiment, can be further integrated with a network, an intranet/internet or a wireless communication means for the control of test apparatus 10 from a remote location.

While test apparatus 10 is described herein in reference to cement slurry compositions under simulated deep downhole oil well conditions, it understood that test sample 5 can be any composition of test sample in which shrinkage and expansion measurements are desired under varying temperature and/or pressure conditions.

The above describes the principal features of the invention. It does not limit its application and as will be apparent to one of ordinary skill in the art, the details of test apparatus 10 can vary with the types of vessel assembly 20, pump 50, thermal instrument 60 and computer 70 are utilized. It is to be understood that the above embodiment is illustrative and that, for example, a number of the functions of the individual systems can be combined. It is similarly understood that test sample 5 can include alternative sealing material compositions.

In operation, as shown in FIGS. 1-5, tube 21 and bottom plug 22 are assembled. The sample containing portion 6 in vessel assembly 20 is filled with approximately 200 ml of a cement slurry sample without contaminating the shoulder where diaphragm 24 seals or the threads. Diaphragm 24 is positioned on the liquid slurry and against the sealing shoulder. A washer or ring 19 is positioned above diaphragm 24 and against the lower mating edge of top plug assembly 25 to seal and isolate test sample 5 in the sample containing portion 6 from incompressible medium 8 in the first chamber 7.

Top plug assembly 25, with piston 31 positioned in bore 39, can be manually connected to tube 21 using handles 29. Medium 8 is added to test vessel 20 through high-pressure ports 28 and fills the first chamber 7 between diaphragm 24 and piston 31. Reservoir 82 can also be used to fill the first chamber 7 with incompressible medium 8. Temperature sensor 64 is connected through one of top ports 28 and the remaining top high-pressure port 28 is securely coupled to pump 50. Thermal device 62 is positioned on vessel 20 for heating and cooling test sample 5.

Medium 9 is added through high-pressure port 28A in plug 26 to fill the second chamber 11 and is preferably coupled to reservoir 82 as a source of medium 9 in fluid source 80. Alternatively, medium 8 and medium 9 in vessel assembly 20 are in direct fluid communication with pump 50. Piston 31 is preferably positioned in the mid-range of top plug assembly 25, but can be adjusted as required to provide additional shrinkage or expansion travel. The LVDT transducer output is connected through high-pressure electrical sensor 37 on the side of tube 27 to data interface device 40A.

Data interface device 40A is programmed for the test profile desired for test sample 5. This includes the calibration of test apparatus 10 using the Data Acquisition Software or similar software in data interface device 40A to synchronize the physical position of the piston at the zero (0) mL position for the accurate measurement of data. Test apparatus 10 is programmed to apply a broad range of test profiles for testing a specific cement composition that is intended to simulate the pressure and temperature conditions at specific downhole depths in an oil well in which that particular cement composition is to be utilized. In one preferred embodiment, test apparatus 10 can provide a rapid temperature and/or pressure ramping to simulate the introduction of the cement slurry test sample 5 at an ambient temperature to the high temperature of deep downhole depths.

Controller 40 initiates the test profile for heating and pressurizing test vessel 20 using thermal device 62 and pump 50. The actual volume changes of the test sample 5 are recorded, using the zero position of piston 31 as a baseline, throughout the testing process, including during and after the setting and curing of the initial cement slurry of test sample 5. The actual test conditions and test data sensed by temperature sensor 64, pump 50 and sensor system 30 are transmitted as data to controller 40 and data interface 40A and/or computer 70. Manual control can also be initiated at controller 40, as necessary. Computer programs, if desired, can also be used to analyze the data collected and stored in computer 70 and/or to present actual test data in a desired format such as a percent of change in volume of test sample 5.

When test sample 5 expands, for example, diaphragm 24, the fixed volume of incompressible medium 8, piston 31, rod 32 and core 35 displace in the direction of the top of vessel assembly 20 and against the balancing pressure of medium 9 in the second chamber 11. Controller 40 maintains incompressible medium 8 at a desired pressure in conjunction with the pressure applied by pump 50 through medium 9 by allowing a controlled volume of medium 9 to be released from the second chamber 11 through port 28A to reservoir 82 of external fluid source 80. The release of a portion of medium 9 sustains the desired pressure applied by medium 9 at a new position of piston 31 in bore 33 that is detected by sensor system 30.

When test sample 5 shrinks during testing due to setting, diaphragm 24 is displaced with test sample 5 in the direction towards the bottom of vessel assembly 20 by the pressure of medium 9 applied through piston 31 and medium 8 in the first chamber 7. Medium 8 fills the additional area left by the shrinkage of test sample 5 and the constant pressure maintained by medium 9 by controller 40, drives piston 31, rod 32 and core 35 in the direction of the bottom of vessel assembly 20. Piston 31 is displaced a distance by the pressure of medium 9 from pump 50 to a new position with the same balance of pressure between incompressible medium 8 and medium 9. In one preferred embodiment, medium 8 is preferably maintained by pump 50 and thermal instrument 60 at the same constant pressure and temperature during testing. Pump 50 preferably sustains the constant pressure of expanding medium 9 in the second chamber 11 by supplying additional medium 9 from pressurized reservoir 82. It is understood, however, that the temperature and pressure observed by test sample 5 can vary depending upon the environment that test sample 5 will actually experience.

Controller 40 will constantly adjust the volume of medium 9 via pump 50 to retain the desired pressure level. When the volume changes of test sample 5 cease for a given period, for example, the displacement of medium 8, piston 31 and medium 9 stabilize and the pressure level set through controller 40 is applied to medium 9 in the new displaced position of piston 31. The process is then repeated, as required, by the changes in volume of test sample 5. This process provides for the direct measurement of the displacement of piston 31 using sensor system 30 and the displacement data then being converted into to volume changes in test sample 5.

In the preferred embodiment of test apparatus 10, medium 9 is an incompressible fluid medium that is directly supplied by one or more pumps 50 to the second chamber 11 from reservoir 82, for example. Pump 50 maintains the balance of pressure on medium 9 such that piston 31 is free to move in response to displacements of incompressible medium 8 due to changes in volume of test sample 5.

In another preferred embodiment, the Data Acquisition and Control System on computer 70 receives basic sample identification information, the programmed test profile parameters, such as starting and completion times, temperature and pressure ramping as well as dwell times and actual measured values for temperature and pressure. Intermediate and final values of expansion or shrinkage as a percentage, along with as many intermediate readings and times as may be desired for analytical purposes, are also entered.

The test is terminated by stopping test operations at controller 40 and/or the flow of test data into data acquisition software programs and temperature and/or controller 40. The cables and tubes are disconnected from vessel 20 and vessel 20 is removed from thermal device 62. Top plug assembly 25, bottom plug assembly 22 and the sample are removed from tube 21 and vessel 20 is properly cleaned.

Although the illustrative embodiments of the present disclosure have been described with reference to the accompanying drawings, it is to be understood that the disclosure is not limited to those specific embodiments and that various other changes and modifications will be apparent to one of ordinary skill in the art without departing from the scope and spirit of the invention which is to be determined with reference to the following claims.

I claim:

1. A test apparatus for the measurement of a change in volume due to the expansion and/or shrinkage of a curable test sample during curing of the sample from a viscous to a solid state, the apparatus comprising:
   a. a pressure vessel assembly housing having a sample-containing portion for receiving the test sample and providing an exposed sample surface;
   b. a flexible barrier seal extending across the sample surface for isolating the test sample in the sample-containing portion;
   c. a piston slidably mounted in a bore in the vessel assembly housing and spaced apart from the barrier seal to define a first fluid-tight chamber for receiving a volume of a first incompressible pressurized fluid medium;
   d. a second chamber defined by the opposite wall of the piston and the vessel housing;
   e. a pressurizing fluid reservoir external to the housing and in fluid communication with the second chamber;
   f. a pump in fluid communication with the second chamber and reservoir, whereby a fluid in the second chamber pressurized by the pump exerts a corresponding pressure on a sample in the sample-containing portion via the piston; and
   g. a sensor assembly operably connected to the piston for measuring changes in the position of the piston resulting from the change in volume of the test sample.

2. The test apparatus of claim 1, wherein the first pressurized incompressible medium is a liquid.

3. The test apparatus of claim 1, wherein the second medium is a liquid.

4. The test apparatus of claim 1, wherein the sensor assembly includes a core and a measuring device, with a coil whereby the movement of the piston is translated to core movement that is sensed by the coil.

5. The test apparatus of claim 1 which further includes heating and cooling means to raise and lower the temperature of the sample.

6. The test apparatus of claim 1 further comprising a computer that includes an indicator for the initial position of the piston in the bore.

7. The test apparatus of claim 1, wherein the external fluid reservoir includes a reservoir fluid level indicator with markings that correlate to the change in volume of the test sample during curing.

8. The test apparatus of claim 1 which further includes a controller that contains test parameters and receives and records test data.

9. The test apparatus of claim 8, wherein the test parameters comprise pressure, temperature, the rate of change of pressure and temperature, and time.

10. A test apparatus for the measurement of the expansion and/or shrinkage of a test sample comprising:
    a vessel assembly housing, one end of which includes a sample-receiving portion;
    a flexible seal extending across the sample-receiving portion to isolate a sample placed therein from the rest of the housing;
    a movable piston sealingly mounted in a bore of the vessel assembly housing and isolating a first pressurized chamber from a second pressurizing chamber in the housing, the first chamber being defined by the flexible seal and one face of the piston, the first chamber being provided with an incompressible fluid, the second chamber being defined by an opposing side of the piston and the end of the housing opposite the sample-receiving portion;
    a source of pressurizing fluid external to the housing and in fluid communication with the second chamber; and
    a sensor assembly that is responsive to movement of the piston and an associated display and recording means for measuring the linear movement of the piston.

11. The test apparatus of claim 10, wherein the piston is a floating piston that is pressure-balanced between the incompressible medium in the first chamber and the second medium in the second chamber and, the piston moves in the bore of the vessel assembly housing in direct correlation to changes in the volume of the test sample, the movement of the piston in the bore being detected by a measuring device.

12. The sensor assembly of claim 10 in which a mechanical linkage extends from the piston through the second chamber to a measuring device.

13. The test apparatus of claim 12, wherein the measuring device indicates the displacement of the piston by the displacement of the pressurized fluid in response to an increase or decrease in the volume of the test sample by the displacement of the flexible seal.

14. The test apparatus of claim 10, which further includes means for heating and cooling the test sample in the vessel assembly to simulate downhole conditions.

15. The test apparatus of claim 14, wherein the functions of the assembly are directed by a computer integrated with the test apparatus.

16. A method for measuring the expansion and/or contraction of a curable test sample comprising the steps of:
    isolating a flowable test sample in a rigid sample-receiving portion of a test vessel;
    securing a flexible seal over an exposed surface of the test sample;
    contacting a surface of the flexible seal opposite the sample surface with a fixed volume of an incompressible pressurized liquid that is maintained in a first chamber in the test vessel by a proximal face of a movable piston that is sealingly positioned in a bore formed in the test vessel;

applying to a distal face of the piston a force by a pressurizing fluid that is contained in a second chamber in the test vessel, whereby the liquid in the first chamber and the fluid in the second chamber are isolated from each other; measuring any movement of the piston during the curing of the sample; and correlating the movement of the piston to a volumetric change of the sample.

17. The method of claim 16, which includes filling the sample-receiving portion of the vessel assembly with a curable cement test sample.

18. The method of claim 16, which includes heating and/or cooling the test sample.

19. The method of claim 16, wherein the pressure of the pressurizing fluid is substantially constant during a test cycle.

20. The method of claim 16, wherein the step of measuring further includes detecting the amount of displacement of the piston using a linear variable displacement transducer (LVDT).

21. The method of claim 16, wherein the step of measuring further includes transmitting the data on the change of volume of the test sample to a controller processor.

22. The method of claim 16, where the correlation of the piston's movement includes transmitting signal data to a computer for at least receiving, processing and recording test data.

23. The method of claim 16 which further includes removing any air entrained in the test sample before securing the flexible seal over the surface of the sample.

24. The method of claim 16 which further includes excluding air from the first and second chambers and from the liquid and fluid contained in said respective chambers.

* * * * *